US007763053B2

(12) United States Patent
Gordon (10) Patent No.: US 7,763,053 B2
(45) Date of Patent: Jul. 27, 2010

(54) IMPLANT FOR CORRECTION OF SPINAL DEFORMITY

(76) Inventor: Jeffrey D. Gordon, 2015 Terry Ave., #313, Seattle, WA (US) 98121

( * ) Notice: Subject to any disclaimer, the term of this patent is extended or adjusted under 35 U.S.C. 154(b) by 1170 days.

(21) Appl. No.: 11/215,725

(22) Filed: Aug. 30, 2005

(65) Prior Publication Data

US 2006/0047282 A1 Mar. 2, 2006

Related U.S. Application Data

(60) Provisional application No. 60/605,548, filed on Aug. 30, 2004.

(51) Int. Cl.
*A61B 17/60* (2006.01)
(52) U.S. Cl. .................. 606/258; 606/105; 606/263; 606/57; 606/86 R; 606/279; 606/259; 623/18.12
(58) Field of Classification Search ........... 606/86 A, 606/907, 54, 55, 56, 57, 58, 59, 246, 250, 606/251, 252, 253, 254, 255, 256, 257, 258, 606/259, 260, 261, 262, 263, 264, 265, 266, 606/267, 268, 269, 270, 271, 272, 273, 274, 606/275, 276, 277, 278, 279, 86 R, 86 B, 606/90, 105; 623/18.12; 600/12
See application file for complete search history.

(56) References Cited

U.S. PATENT DOCUMENTS

| 2,702,031 | A | | 2/1955 | Wenger | |
|---|---|---|---|---|---|
| 3,976,060 | A | * | 8/1976 | Hildebrandt et al. | ........ 606/241 |
| 4,047,523 | A | | 9/1977 | Hall | |
| 4,448,191 | A | | 5/1984 | Rodnyansky et al. | |
| 5,147,360 | A | | 9/1992 | Dubousset | |
| 5,290,289 | A | | 3/1994 | Sanders et al. | |
| 5,490,851 | A | | 2/1996 | Nenov et al. | |
| 5,704,939 | A | * | 1/1998 | Justin | ........................ 606/63 |
| 6,251,111 | B1 | * | 6/2001 | Barker et al. | ............. 606/86 A |
| 6,299,613 | B1 | | 10/2001 | Ogilvie et al. | |
| 6,551,320 | B2 | | 4/2003 | Lieberman | |
| 6,565,576 | B1 | * | 5/2003 | Stauch et al. | ............... 606/105 |
| 6,796,984 | B2 | * | 9/2004 | Soubeiran | ................... 606/300 |
| 6,849,076 | B2 | | 2/2005 | Blunn et al. | |
| 2004/0030395 | A1 | * | 2/2004 | Blunn et al. | ............ 623/18.12 |
| 2004/0106921 | A1 | * | 6/2004 | Cheung et al. | ................ 606/61 |
| 2005/0055025 | A1 | | 3/2005 | Zacouto et al. | |
| 2006/0009767 | A1 | * | 1/2006 | Kiester | ........................ 606/61 |
| 2006/0058792 | A1 | * | 3/2006 | Hynes | ......................... 606/61 |
| 2009/0112262 | A1 | * | 4/2009 | Pool et al. | ................... 606/246 |

OTHER PUBLICATIONS

Nachemson, A., Elfstrom G., "Intravital Wireless Telemetry of Axial Forces in Harrington Distraction rods in Patients with Idiopathic Scoliosis", Journal of Bone & Joint Surgery, 1971, 53:445-465.

* cited by examiner

*Primary Examiner*—Eduardo C Robert
*Assistant Examiner*—Jan Christopher Merene
(74) *Attorney, Agent, or Firm*—Taylor & Aust, P.C.

(57) ABSTRACT

A device for correction of a spinal deformity. In one embodiment, the device includes a cable having a first end portion, and an opposite, second end portion attachable to a vertebra, and means for adjusting the tension of the cable so as to impose a corrective displacement on the vertebra.

21 Claims, 11 Drawing Sheets

Fig. 15　　　　Fig. 16

IMPLANT FOR CORRECTION OF SPINAL DEFORMITY

CROSS-REFERENCE TO RELATED PATENT APPLICATION

This application claims priority to and the benefit of, pursuant to 35 U.S.C. §119(e), U.S. provisional patent application Ser. No. 60/605,548, filed Aug. 30, 2004, entitled "Implant For Correction Of Spinal Deformity," by Jeffrey D. Gordon, which is incorporated herein by reference in its entirety.

FIELD OF THE INVENTION

The present invention generally relates to a device for treatment of spine disorders, and in particular to the utilization of an implant to impose a corrective displacement on a vertebra of a patient so as to incrementally correct abnormal spinal curvature(s) of the patient.

BACKGROUND OF THE INVENTION

Scoliosis is a spinal deformity that has an abnormal lateral curvature of the spine when viewed from a posterior perspective. The abnormal curvature of the spine is commonly associated with abnormal spinal rotation causing ribs to protrude posteriorly into what is commonly referred to as "rib hump". The scoliosis is classified with infantile scoliosis and adolescent idiopathic scoliosis. The adolescent idiopathic scoliosis is the most prevalent type of scoliosis which develops during adolescence in an otherwise healthy patient and typically ceases at the onset of skeletal maturity. The cause of the disease is presently unknown.

Currently, surgical treatments of a spinal curvature deformity involve manipulation of the spinal column by attaching a correction device and then fusion of the spine. One such system, used primarily for scoliosis, is the Cotel-Dubousset system, as disclosed in U.S. Pat. No. 5,147,360 to Dubousset, which is understood to the use of rigidly attaching metal rods to the spine with plates and screws. The metal rods are then manipulated during the surgical procedure in an attempt to straighten the abnormal curvatures and reduce the rotation of the spinal column. The spine is then fused with a bone graft, typically requiring extensive discectomies, removal of spinous processes as the bone graft harvest, and injury to the spine itself to induce bleeding for improving the bone fusion. It is believed that the surgery is arduous, invasive, and has an array of potential complications including excessive blood loss. The discs above and below the fusion zone are in jeopardy of degeneration due to the increased biomechanical demands placed on them. Also, flat back syndrome could be problematic if normal lordosis and kyphosis are not restored. Recovery could be a lengthy and painful process. Even a successful procedure rarely results in a normal spinal curvature and the patient is left with an immobile spinal section.

A flaw in the conventional implants for correction of the spinal curvature deformity is that the implants are usually of a part of the load path of the spinal column. For example, it is understood that the Cotel-Dubousset system rigidly attaches stiff stainless steel rods to the spine. For a structure having two members placed in parallel, it relies primarily on the stiffest member for transmission of a load. Therefore, loads exerted on an instrumented spine are transferred through the implant instead of through the spine. Spinal loads could be large, and the geometry of the implants used is such that they may not support such large loads indefinitely. Fatigue failure of the implant occurs if fusion is delayed.

A further disadvantage of the conventional implants for correction of the spinal curvature deformity is the potential for neurologic damage. It has been shown that loads required for correction of the spinal curvature deformity during the surgery warrant concern for spinal cord trauma. For this reason, nerve functions are usually monitored during the surgery. Even after the surgery, the spinal loads could be large enough to cause nerve damages.

Additionally, viscoelastic properties of the spinal structures including the intervertebral discs, ligaments, nerves, muscles and other connective tissues have a time-dependent relationship between force and displacement: the stiffness of viscoelastic structures decreases with time under action of a sustained force. Stress-relaxation and creep are manifestations of viscoelasticity. The creep is gradual displacements under the action of the sustained force, while the stress-relaxation is gradual reductions of an internal force (resistance) under the action of an imposed displacement. It has been shown that dramatic stress-relaxation occurs within minutes of spinal curvature correction procedures. However, stiff instrumentation provides negligible additional correction even though resistive forces in the spine are decreasing.

Therefore, a heretofore unaddressed need exists in the art to address the aforementioned deficiencies and inadequacies.

SUMMARY OF THE INVENTION

In one aspect, the present invention relates to a device for correction of a spinal deformity. In one embodiment, the device includes a cable having a first end portion, and an opposite, second end portion, and a tension member having a cylindrical magnet, a leadscrew and a body. In one embodiment, the leadscrew has a helically threaded exterior surface, an interior surface defining a bore for housing the cylindrical magnet rigidly, an axis therethrough the bore, a first end and an opposite, second end, and a length, $L_2$, defined therebetween. The body has a first end portion and an opposite, second end portion defining a cylindrical chamber therebetween, a longitudinal axis therethrough the cylindrical chamber, a U-shape cut formed in the first end portion, and a length, $L_1$, defined therebetween the first end portion and the second end portion, where $L_1 > L_2$. In one embodiment, the cylindrical chamber has a first chamber portion and a second chamber portion neighboring to the first chamber portion. The first chamber portion and the second chamber portion are sized with a diameter, $d_1$, and $d_2$, respectively, where $d_2 > d_1$ such that a step is formed at the junction of the first chamber portion and the second chamber portion. The first chamber portion is helically threaded for engaging with the leadscrew such that when the leadscrew is received in the cylindrical chamber, the axis of the leadscrew is substantially coincident with the longitudinal axis of the body and the leadscrew is capable of moving back and forth along the longitudinal axis as being rotated around the longitudinal axis. In one embodiment, the tension member further has a first cap and a second cap attached to the first end and the second end of the leadscrew, respectively. The second cap is sized to fit the second chamber portion of the cylindrical chamber such that as assembled, the second cap prevents the leadscrew from moving out of the cylindrical chamber of the body of the tension member.

Furthermore, the device includes a shackle. In one embodiment, the shackle is formed in a clevis-shape and has a first end portion, a second end portion and a body portion defined therebetween, where in use the first end portion and the second end portion are secured to a pelvic bone, and the body portion is received in the U-shape cut of the body of the tension member such that the tension member is capable of rotating around a first axis and a second axis perpendicular to the first axis, respectively. In one embodiment, the first axis and the second axis are perpendicular to the axis of the body of the tension member.

Moreover, the device includes a first engaging member mechanically engaging the first end portion of the cable with the tension member. In one embodiment, the first engaging member includes a ball-and-socket joint mechanism. The first engaging member has a swaged ball attached to the first end portion of the cable, and a pivot cap having a shoulder and a hole formed on the shoulder. As assembled, the first end portion of the cable is received through the hole of the pivot cap and the pivot cap is attached to the first end cap of the tension member such that the swaged ball articulates with the shoulder of the pivot cap, and thus rotating the leadscrew around its axis does not cause the cable to rotate and twist.

Additionally, the device includes a second engaging member arranged, in use, mechanically engaging the second end portion of the cable with a vertebra such that the tension of the cable is adjustable for imposing a corrective displacement on the vertebra. In one embodiment the second engaging member has a bone screw having a screw head, at least one spherical recess formed on the screw head, a hole formed through the at least one spherical recess, and a body portion having helical threads for threading into the vertebra, a ball having a hole formed therethrough, and a crimp. As assembled, the second end portion of the cable is received through the hole in the bone screw and the hole formed in the ball, respectively, and secured by the crimp such that a change in angulation between the tension member and the vertebra is accommodated by articulation of the ball with the spherical recess. In another embodiment, the second end portion of the cable is formed with a loop portion, and the second engaging member has a pair of bone screws attached to the vertebra, a rod connected the pair of bone screws, and a crimp. As assembled, the loop portion of the second end portion of the cable engages with the rod and is secured with the crimp.

The device also includes means for rotating the leadscrew of the tension member around the axis of the body of the tension member. In one embodiment, the rotating means comprises an actuator. The actuator has a first axle and a second axle each having a first end and a second end, a first pulley and a second pulley mounted onto the second end of the first axle and the second end of the second axle, respectively, a cylindrical magnet magnetized diametrically and symmetrically formed on the second axle, a crank attached to the first end of the first axle such that when a torque is applied to the crank to cause the first axle to rotate, a torque is simultaneously applied to the first pulley, and a belt engaging with the first pulley and the second pulley for transferring torques from the first pulley to the second pulley so as to rotate the cylindrical magnet.

In operation, the actuator is positioned such that when the cylindrical magnet of the actuator rotates, a magnetic filed generated by the cylindrical magnet of the actuator causes the cylindrical magnet of the tension member to rotate, which in turn causes the leadscrew of the tension member to rotate so as to cause the tension member to move from a first state to a second state that is different from the first state. In one embodiment, the first state of the tension member is characterized by an angle, $\alpha$, of the axis of the body of the tension member relative to a horizontal axis, and the second state of the tension member is characterized by an angle, $\beta$, of the axis of the body of the tension member relative to the horizontal axis, wherein $0 \leq \alpha < \pi/2$, $0 \leq \beta < \pi/2$, and $\beta \neq \alpha$.

In one embodiment, the cable is made of a biocompatible material. The biocompatible material includes a polymer, a composite, a metal, an alloy, or any combination thereof. In one embodiment, the cable is coated with a material to reduce abrasion and adhesion of biologic tissues.

In another aspect, the present invention relates to a device for correction of a spinal deformity. In one embodiment, the device includes a cable having a first end portion, and an opposite, second end portion, a tension member, a first engaging member mechanically engaging the first end portion of the cable with the tension member, a second engaging member mechanically engaging the second end portion of the cable with a vertebra, and a third engaging member mechanically engaging the tension member with a pelvic bone.

In one embodiment, the tension member has a leadscrew which has a head, a shank extending from the head, and a threaded portion extending from the shank. The tension member further has a one-way clutch coupled with the shank such that when rotating in one of the clockwise and counterclockwise directions, the one-way clutch engages with the shank, and when rotating in the other of the clockwise and counterclockwise directions, the one-way clutch freewheels on the shank. The tension member also has a body having an interior surface complementarily threaded for receiving the leadscrew, an axis, a first end portion, an opposite, second end portion, and a U-shape cut and a hole formed in the second end portion, where the hole of the body has an axis perpendicular to the axis. Additionally, the tension member has a toggle. The toggle, in one embodiment, has a first end portion and an opposite, second end portion defining a chamber therebetween for housing the one-way clutch rigidly, a pair of wings radially protruding from the second end portion, and a hole formed on the first end portion.

In one embodiment, the first engaging member includes a ball-and-socket joint mechanism. The first engaging member has a swaged ball attached to the first end portion of the cable, and a pivot cap having a shoulder and a hole formed on the shoulder. As assembled, the first end portion of the cable is received through the hole of the pivot cap and the pivot cap is attached to the head of the leadscrew of the tension member such that the swaged ball articulates with the shoulder of the pivot cap, and thus rotating the leadscrew around its axis does not cause the cable to rotate and twist. In another embodiment, the first end portion of the cable is formed with a loop portion, and the first engaging member has a pin, and a crimp. As assembled, the loop portion of the first end portion of the cable engages with the pin and is secured with the crimp.

The second engaging member in one embodiment, has a bone screw having a screw head, at least one spherical recess formed on the screw head, a hole formed through the at least one spherical recess, and a body portion having helical threads for threading into the vertebra, a ball having a hole formed therethrough, and a crimp. As assembled, the second end portion of the cable is received through the hole in the bone screw and the hole formed in the ball, respectively, and secured by the crimp such that a change in angulation between the tension member and the vertebra is accommodated by articulation of the ball with the spherical recess. In another embodiment, the second end portion of the cable is formed with a loop portion, and the second engaging member comprises a pair of bone screws attached to the vertebra, a rod connected with the pair of bone screws, and a crimp. As assembled, the loop portion of the second end portion of the cable engages with the rod and is secured with the crimp.

In one embodiment, the third engaging member includes a clevis-shape shackle. The clevis-shape shackle in one embodiment has a first end portion, a second end portion and a body portion defined therebetween, where in use the first end portion and the second end portion are secured to the pelvic bone, and the body portion is received in the U-shape cut of the body of the tension member and secured by placing a pin into the hole of the body of the tension member such that the tension member is capable of rotating around a first axis and a second axis, respectively. In one embodiment, the first axis is substantially coincident with the axis of the hole of the body of the tension member, and wherein the second axis is perpendicular to the first axis and the axis of the body of the tension member, respectively.

In operation, by pressing alternately on each of the pair of wings of the toggle of the tension member, the one-way clutch rotates alternately in the clockwise and counterclockwise directions thereby causing the leadscrew to rotatably advance into the body so as to cause the tension member to move from a first state to a second state that is different from the first state, whereby the tension of the cable is adjustable for imposing a corrective displacement on the vertebra. In one embodiment, the first state of the tension member is characterized by an angle, $\alpha$, of the axis of the body of the tension member relative to a horizontal axis, and the second state of the tension member is characterized by an angle, $\beta$, of the axis of the body of the tension member relative to the horizontal axis, wherein $0 \leq \alpha < \pi/2$, $0 \leq \beta < \pi/2$, and $\beta \neq \alpha$.

In yet another aspect, the present invention relates to a device for correction of a spinal deformity. In one embodiment, the device includes a cable having a first end portion, and an opposite, second end portion attachable to a vertebra, means for adjusting the tension of the cable so as to impose a corrective displacement on the vertebra, and means for attaching the body to a pelvic bone. In one embodiment, the adjusting means comprise a screw having a threaded portion and engaged with the first end portion of the cable, and a body having an interior surface complementarily threaded for receiving the screw such that when the screw rotatably advances into the body, the tension of the cable is adjusted.

In yet a further aspect, the present invention relates to a device for correction of a spinal deformity. In one embodiment, the device includes a tension adjusting member having a first end, a second end, and a body defined therebetween the first end and the second end. The device further includes a tension member having a first end portion, a second end portion and a body portion defined therebetween the first end portion and the second end portion, and movably engaged with the body of the tension adjusting member such that the first end portion of the tension member is movable relative to the first end of the tension adjusting member for adjusting the tension of the tension member. In use, the second end portion of the tension member is to be secured to a vertebra and the first end of the tension adjusting member is to be secured to a pelvic bone so that when the first end portion of the tension member moves away from or toward to the first end of the tension adjusting member, the tension of the tension member is adjusted so as to impose a corrective displacement on the vertebra.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE PREFERRED EMBODIMENTS

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The description will be made as to the embodiments of the present invention in conjunction with the accompanying drawings 1-16. In accordance with the purposes of this invention, as embodied and broadly described herein, this invention, in one aspect, relates to an implant for a surgical correction of abnormal spinal curvatures by imposing corrective displacements on abnormal spinal vertebras. For ease of understanding, the present invention is described with specific reference to scoliosis. However, the present invention disclosed herein is generally applicable to all classifications of spinal curvature disorders, including lordosis and kyphosis in the spine.

Figure 1A:
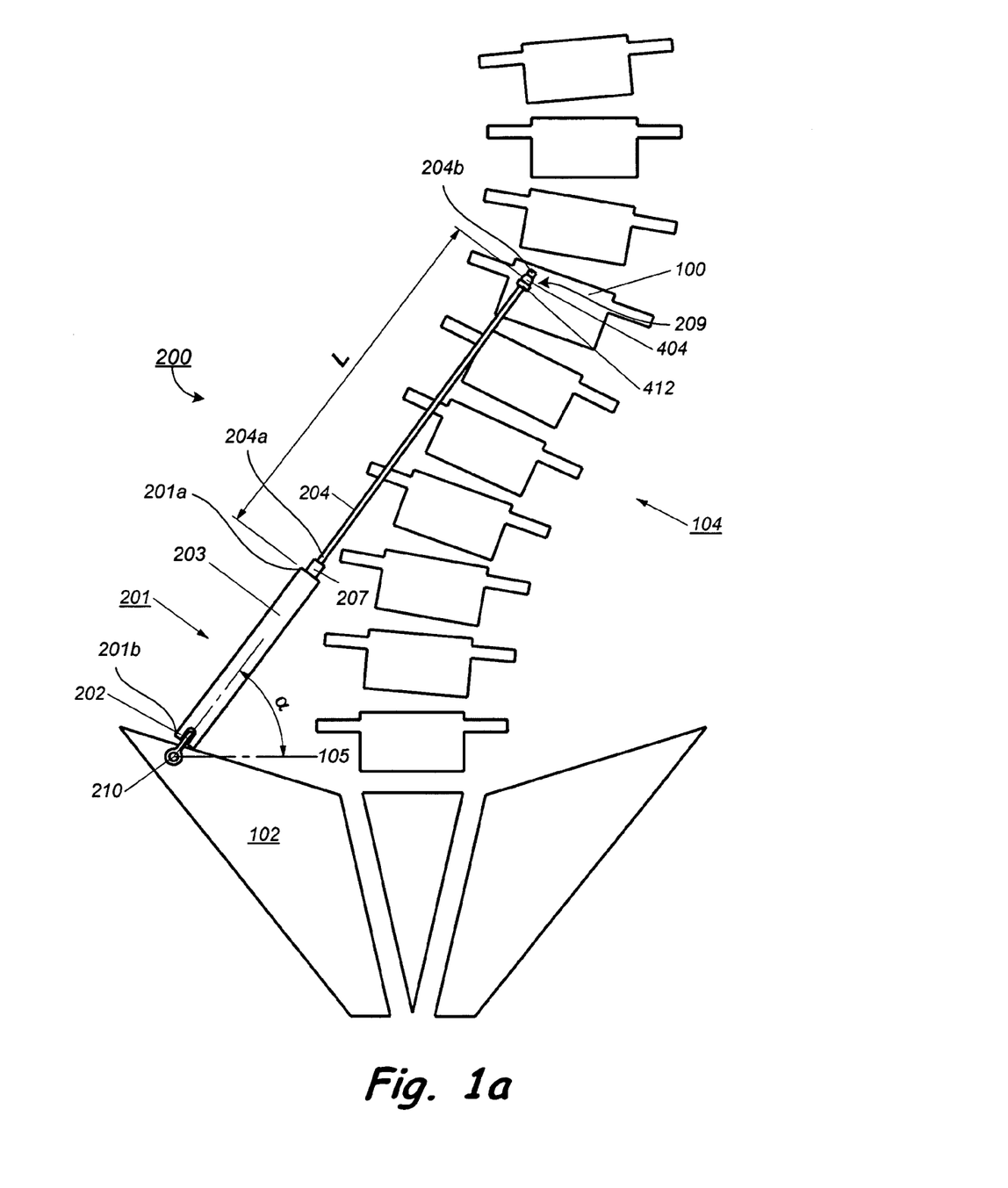
FIG. 1a shows schematically a posterior view of a scoliotic human spine with an implanted device according to one embodiment of the present invention.

Referring to FIG. 1a, a posterior view of a scoliotic spine 104 of a patient having an abnormal spinal curvature is shown schematically, where a device (implant) 200 is attached to a pelvic bone 102 and a vertebra 100 of the patient, respectively, according to one embodiment of the present invention. The invented device 200, as described in details below, includes a tension member 201, a cable 204 having a first end portion 204a and an opposite, second end portion 204b, a first engaging member 207 mechanically engaging the first end portion 204a of the cable 204 with the tension member 201, a second engaging member 209 mechanically engaging the second end portion 204b of the cable 204 with the vertebra 100, and a shackle 202 mechanically engaging the tension member 201 with the pelvic bone 102. The tension of the cable 204 is adjustable for imposing a corrective displacement on the vertebra 100 to correct the abnormal spinal curvature of the patient. The shackle 202 is mounted to the pelvic bone 102 with a shackle clevis screw 210. In one embodiment, the second engaging member 209 has a bone screw 412 and a ball 404 adapted for securing the second end portion 204b of the cable 204 to the vertebra 100. As implanted in relation to a pelvic bone 102 and a vertebra 100, the tension member 201 forms an initial angle, $\alpha$, relative to a horizontal plane 105, hence defining an initial distance (length), L, between a first end 201a of the tension member 201 and the bone screw 412, where $0 \leq \alpha < \pi/2$.

Figure 1B:
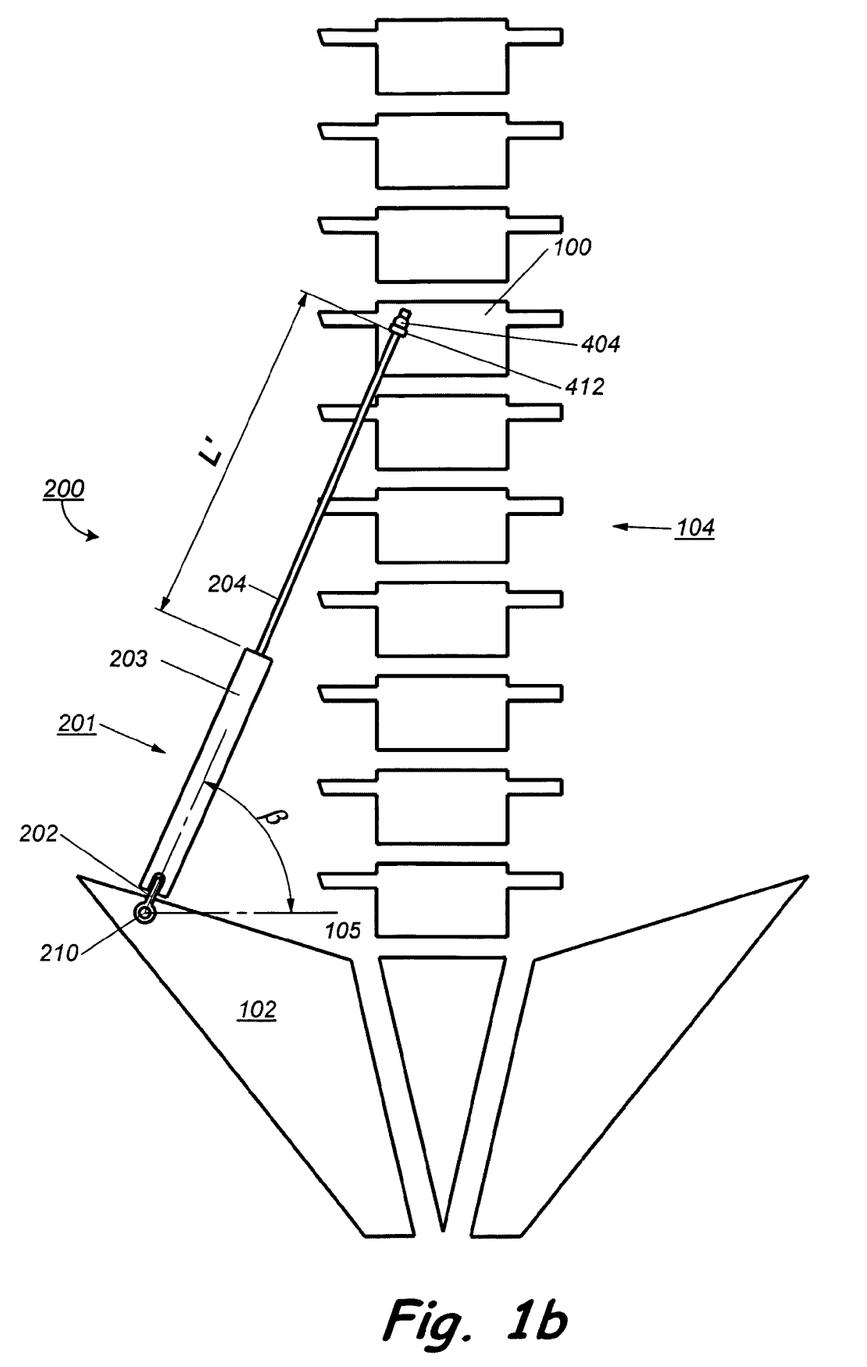
FIG. 1b shows schematically a posterior view of a corrected human spine with the implanted device shown in FIG. 1b.

FIG. 1b shows a posterior view of the spine 104 of the patient after correction of the abnormal spinal curvature with the implanted device 200. As shown in FIG. 1b, after the correction, the angle between the tension member 201 and the horizontal plane 105 is indicated by $\beta$, where $0 \leq \beta < \pi/2$, and $\beta \neq \alpha$. In this exemplary embodiment, $\beta < \alpha$. The distance between the first end 201a of the tension member 201 and the bone screw 412 has been changed from L to L'. L' may be greater or less than L. In the embodiment shown in FIG. 1b, L'<L.

Figure 2:
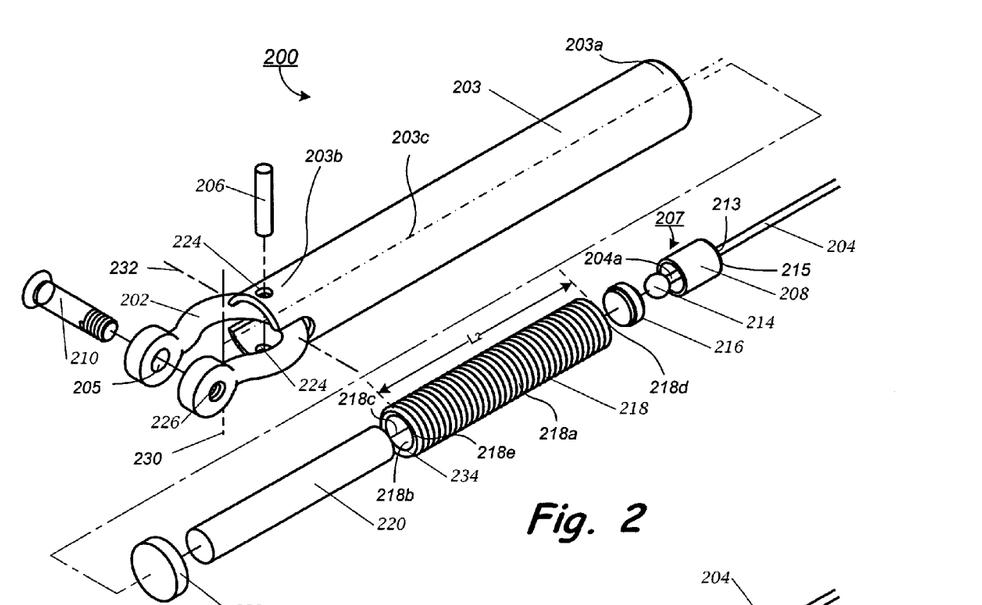
FIG. 2 shows a perspective exploded view of a device according to one embodiment of the present invention.
Figure 3:
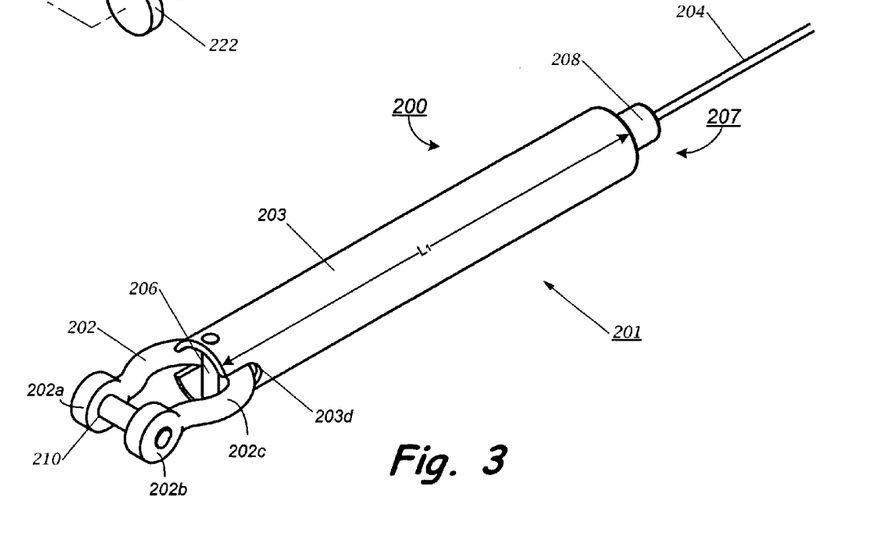
FIG. 3 shows a perspective view of the device shown in FIG. 2.
Figure 6:
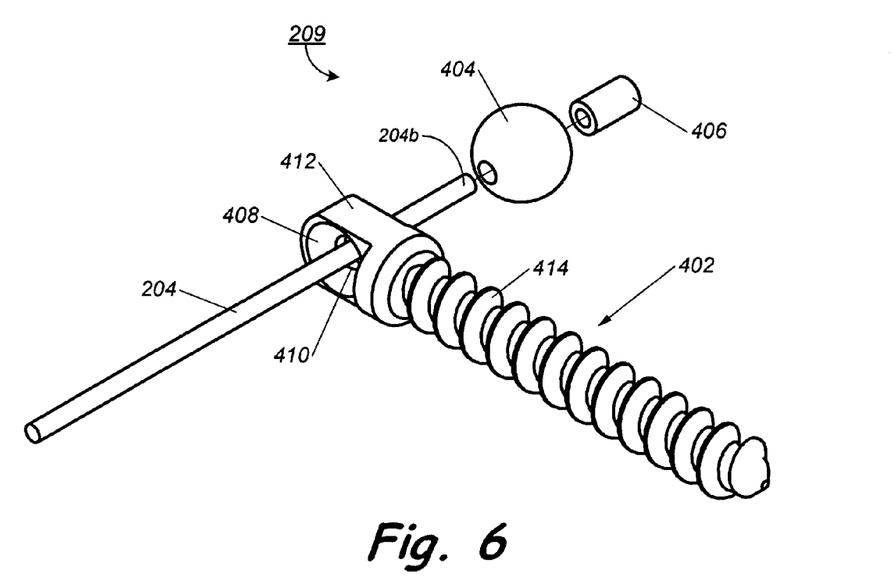
FIG. 6 shows a perspective exploded view of a second engaging member according to one embodiment of the present invention.
Figure 7:
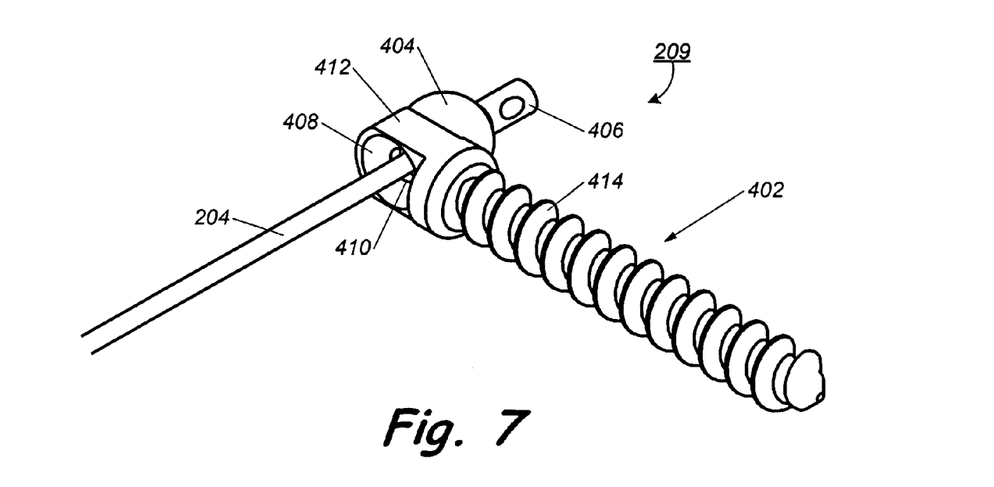
FIG. 7 shows a perspective view of the second engaging member shown in FIG. 6.
Figure 8:
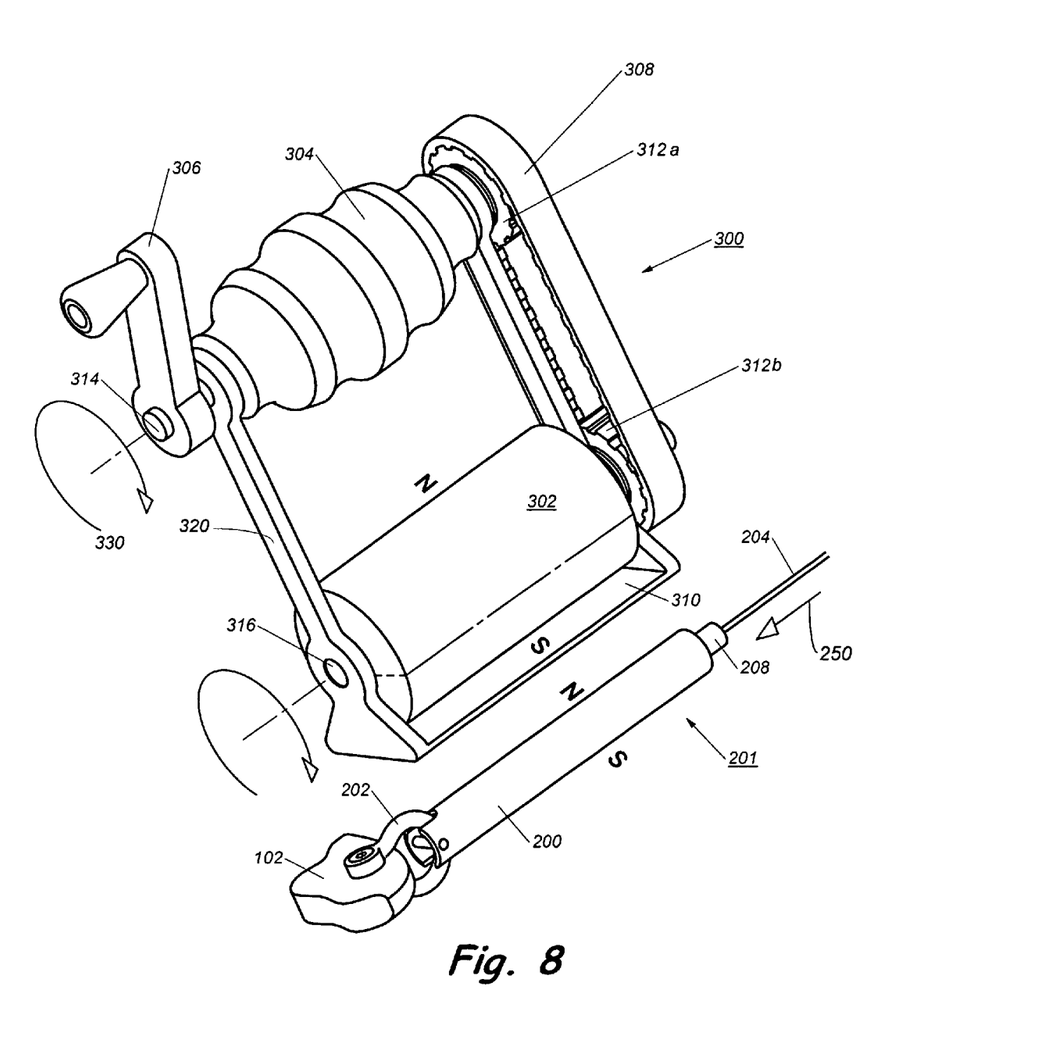
FIG. 8 shows a perspective view of an actuator and a device according to one embodiment of the present invention.

Referring now to FIGS. 2-12 and first to FIGS. 2 and 3, device 200 is shown to have the tension member 201, the cable 204, the first engaging member 207 and the second engaging member 209, and the third engaging member 202 according to one embodiment of the present invention. The cable 204 has a first end portion 204a and an opposite, second end portion 204b. The tension member 201 has a cylindrical magnet 220 magnetized diametrically. In one embodiment, the cylindrical magnet 220 has a first semi-cylindrical portion and an opposite, second semi-cylindrical portion. The first semi-cylindrical portion and the second semi-cylindrical portion of the cylindrical magnet 220 are magnetized as a north pole, N, and a south pole, S, respectively, as shown in FIG. 8.

The tension member 201 further has a leadscrew 218. In one embodiment, the leadscrew 218 has a helically threaded exterior surface 218a and an, interior surface 218b, a first end 218d and an opposite, second end 218e, a cylindrical bore 234 defined by the interior surface 218b and between the first end 218d and the second end 218e, an axis 218c therethrough the cylindrical bore 234, and a length, $L_2$, defined by the first end 218d and the second end 218e. The cylindrical bore 234 is adapted for housing the cylindrical magnet 220 rigidly. As assembled, the cylindrical magnet 220 and the leadscrew 218 are fixedly engaged such that the cylindrical magnet 220 does not rotate relative to the leadscrew 218 in operation. In one embodiment, the engagement of the cylindrical magnet 220 with the leadscrew 218 is implemented by an anti-rotation means, for example, an adhesive or a mechanical interlock (not shown). After the cylindrical magnet 220 is received into the cylindrical bore 234 of the leadscrew 218, the first end 218d and the second end 218e of the leadscrew 218 are hermetically sealed by a first cap 216 and a second cap 222, respectively. The sealing process, in one embodiment, is performed with a laser welding. Other sealing methods can also be used to practice the present invention.

The tension member 201 also includes a body 203. The body 203 has a first end portion 203a and an opposite, second end portion 203b defining a cylindrical chamber 229 therebetween, a longitudinal axis 203c therethrough the cylindrical chamber 229, a U-shape cut 203d formed in the second end portion 203b, and a length, $L_1$, defined between the first end portion 229a and the second end portion. In one embodiment, $L_1 > L_2$. The cylindrical chamber 229 has a first chamber portion 229a and a second chamber portion 229b neighboring to the first chamber portion 229a. The first chamber portion 229a and the second chamber portion 229b are sized with a diameter, $d_1$, and $d_2$, respectively. In one embodiment, $d_2 > d_1$, and thus a step 229c is formed at the junction of the first chamber portion 229a and the second chamber portion 229b. In one embodiment, the first chamber portion 229a is helically threaded for engaging with the leadscrew 218. When the leadscrew 218 is received in the cylindrical chamber 229, the axis 218c of the leadscrew 218 is substantially coincident with the axis 203c of the body 203, and the leadscrew 218 is capable of moving back and forth along the axis 203c of the body 203 as being rotated around the axis 203c of the body 203 of the tension member 201. In one embodiment, the second cap is sized to fit the second chamber portion 229b of the cylindrical chamber 229 such that as assembled, the second cap prevents the leadscrew 218 from moving out of the cylindrical chamber 229 of the body 203 of the tension member 201. The second end cap maintains concentricity with and therefore alignment of the leadscrew 218 relative to the body 203 of the tension member 201.

The first engaging member 207 mechanically engages the first end portion 204a of the cable 204 with the tension member 201. In one embodiment as shown in FIG. 2, the first engaging member 207 has a ball-and-socket joint mechanism in which a swaged ball 214 is fixedly attached to the first end portion 204a of the cable 204. The first engaging member 207 further has a pivot cap 208 that has a shoulder 215, in which a hole 213 is formed. As assembled, the first end portion 204a of the cable 204 attached to the swaged ball 214 is received through the hole 213 of the pivot cap 208 and the pivot cap 208 is then fixedly attached to the first end cap 216 of the tension member 201 by welding or other attaching means. In this embodiment, the swaged ball 214 articulates with the shoulder 215 of the pivot cap 208, and thus rotating the leadscrew 218 around its axis 218c does not cause the cable 204 to rotate and twist.

The second engaging member 209 for mechanically engaging the second end portion 204b of the cable 204 with the vertebra 100, in one embodiment, as shown in FIGS. 6 and 7, includes a bone screw 402 having a screw head 412, two spherical recesses 408 formed on two sides of the screw head 412, respectively, a hole 410 formed through the two spherical recesses 408, and a body portion 414 having helical threads for threading into the vertebra 100, a ball 404 having a hole formed therethrough, and a crimp 406. As assembled, the second end portion 204b of the cable 204 is received through the hole 410 in the bone screw 402 and the hole formed in the ball 404, respectively, and secured by the crimp 406 such that a change in angulation between the tension member 201 and the vertebra 100 is accommodated by articulation of the ball 404 with the spherical recess 408.

Figure 11:
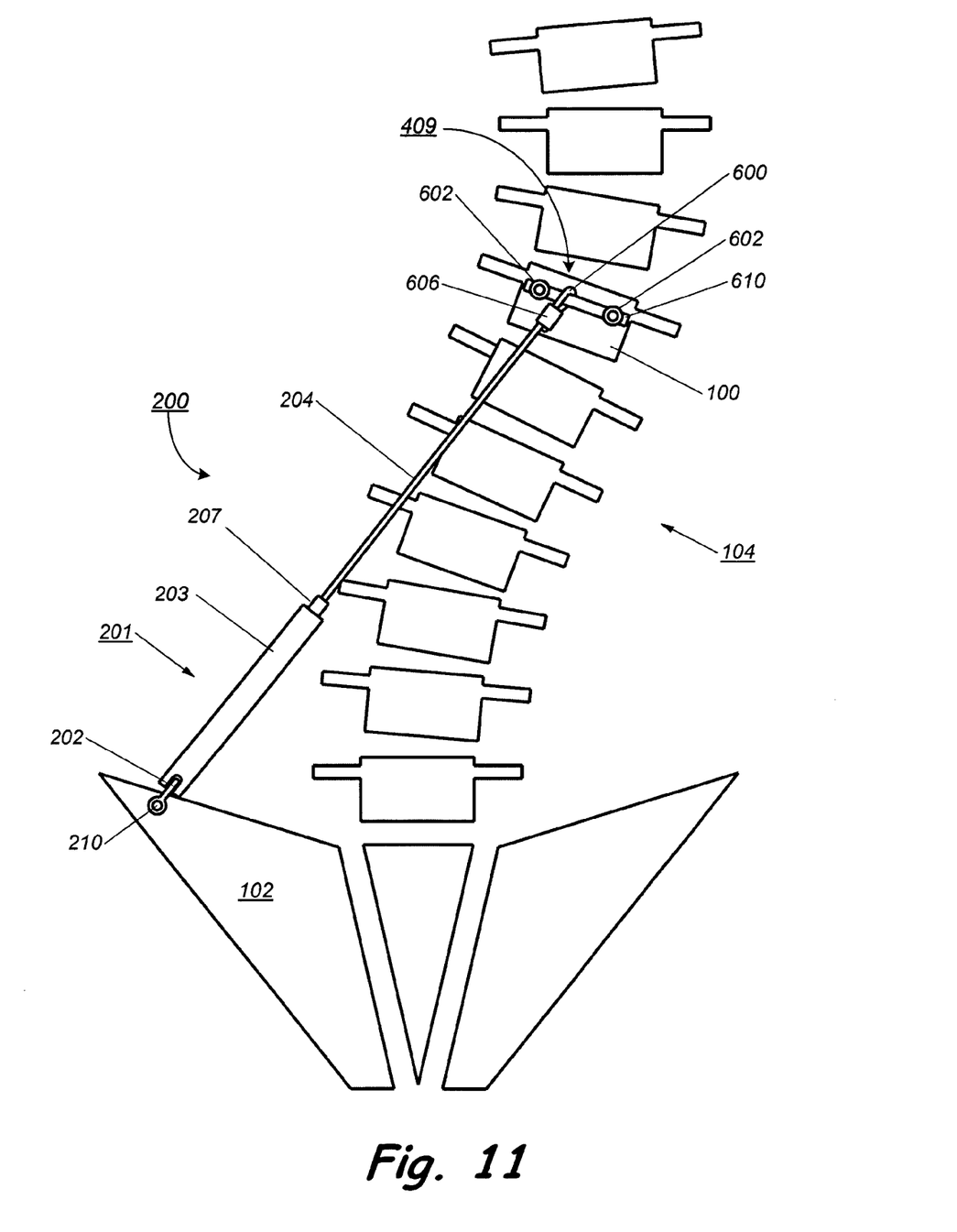
FIG. 11 shows schematically a posterior view of a scoliotic human spine with an implanted device according to another embodiment of the present invention.
Figure 12:
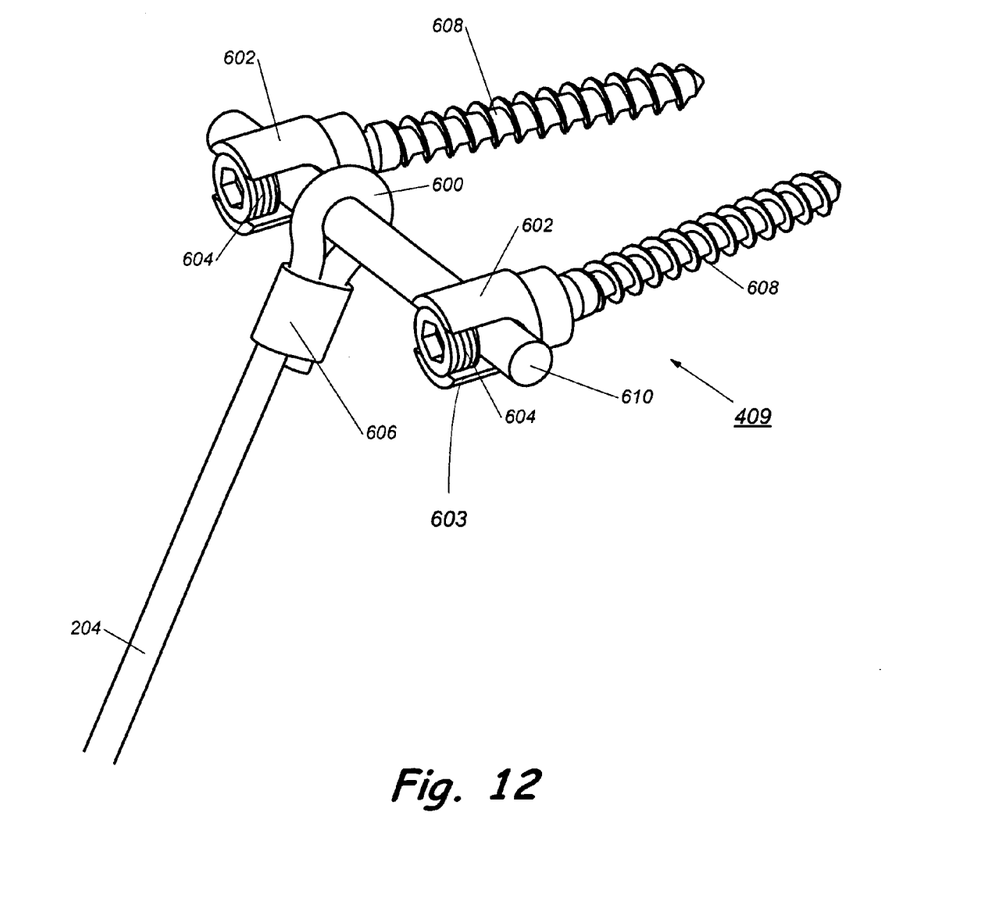
FIG. 12 is a perspective view of an alternative embodiment of the second engaging member.

In another embodiment, as shown in FIGS. 11 and 12, the second engaging member 409 has a pair of bone screws 602 attached to the vertebra 100, a rod 610 engaged with the pair of bone screws 602, and a crimp 606. The bone screws 602 has a polyaxial screw head 603 and a helical threaded body 608 extending from the polyaxial screw head 603. As assembled, a loop portion 600 formed in the second end portion 204b of the cable 204 engages with the rod 610 and is secured with the crimp 606. In one embodiment, the rod 610 is secured to the pair of bone screws 602 by threading a pair of screw caps 604 into the polyaxial screw heads 603 of the pair of the bone screws 602, respectively. The use of multiple bone screws enhances fixation of the device 200 to the spine 204.

The third engaging member 202 for mechanically engaging the tension member 201 with the pelvic bone 102 in one embodiment includes a shackle 202. As shown in FIGS. 2-5, the shackle 202 is formed in a clevis-shape and has a first end portion 202a, a second end portion 202b and a body portion 202c defined therebetween. Holes 205 and 226 are formed in the first end portion 202a and the second end portion 202b, respectively. In one embodiment, one of the holes 205 and 226 is helically threaded for receiving a clevis screw 210. The body portion 202c is received in the U-shape cut 203d of the body 203 of the tension member 201 and secured by placing a pin 206 into a hole 224 formed in the second end portion 203b of the body 203 of the tension member 201. The tension member 201 is not rigidly attached to the shackle 202, but is capable of rotating around a first axis 230 and a second axis 232 perpendicular to the first axis 230, respectively. In one embodiment, the first axis 230 is substantially coincident with an axis 230 of the hole 224 in the body 203 of the tension member 201. The first axis 230, the second axis 232 and the axis 203c of the body 203 of the tension member 201 are perpendicular to each other. In this embodiment, the shackle 202 allows the tension element 201 to rotationally orient itself to a relatively straight path toward the spinal attachment site and causes changes in angulation of the tension element 201 relative to the horizontal plane 105 as indicated by angles α and β in FIGS. 1a and 1b, respectively. In one embodiment, the first end portion 202a and the second end portion 202b are secured to the pelvic bone 102. As shown in FIGS. 1a and 1b, a hole is drilled into the pelvic bone 102, the clevis screw 210 is then fed through a hole 205 formed on the first end portion 202a and the hole drilled in the pelvic bone 102, and threaded into a threaded shackle hole 226 formed in the second end portion 202b to secure the shackle 202 to the pelvis bone 102.

The device 200 also includes means for rotating the leadscrew 218 of the tension member 201 around the axis 203c of the body 203 of the tension member 201. In one embodiment, the rotating means includes an actuator. As shown in FIG. 8, actuator 300 has a first axle 314 and a second axle 316 parallelly attached to a frame 320 that has a support flange 310. Each of the first axle 314 and the second axle 316 has a first end and a second end. The actuator 300 further has a first pulley 312a and a second pulley 312b rigidly mounted onto the second end of the first axle 314 and the second end of the second axle 316, respectively. The actuator 300 also has a cylindrical magnet 302 magnetized diametrically and symmetrically formed on the second axle 316. As shown in FIG. 8, the cylindrical magnet 302 has a north pole, N, and a south pole, S. Additionally, the actuator 300 has a crank 306 that is fixedly attached to the first end of the first axle 314 such that when a torque is applied to the crank 306 to cause the first axle 314 to rotate, a torque is simultaneously applied to the first pulley 312a. Moreover, the actuator 300 has a belt 308 engaging with the first pulley 312a and the second pulley 312b for transferring torques from the first pulley 312a to the second pulley 312b so as to rotate the cylindrical magnet 302.

Figure 4:
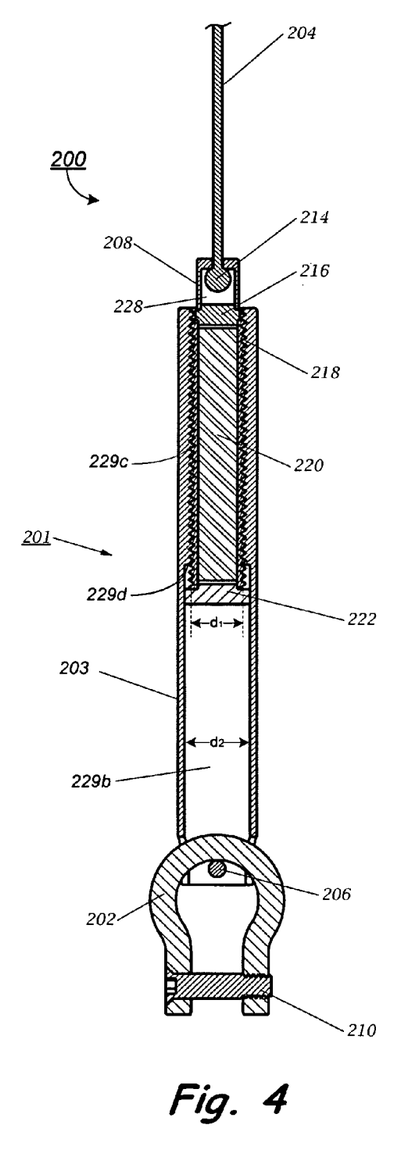
FIG. 4 shows a sectioned view of the device shown in FIG. 2 in an extended configuration.
Figure 5:
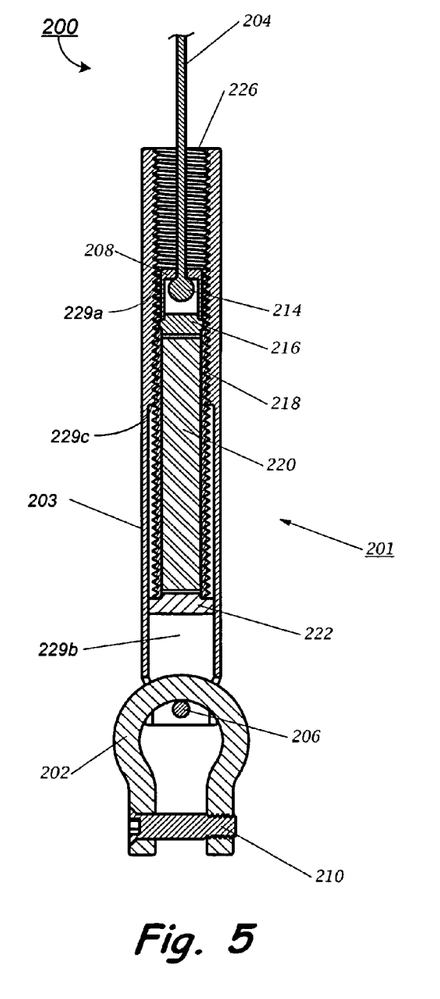
FIG. 5 shows a sectioned view of the device shown in FIG. 2 in a collapsed configuration.
Figures 9, 10:
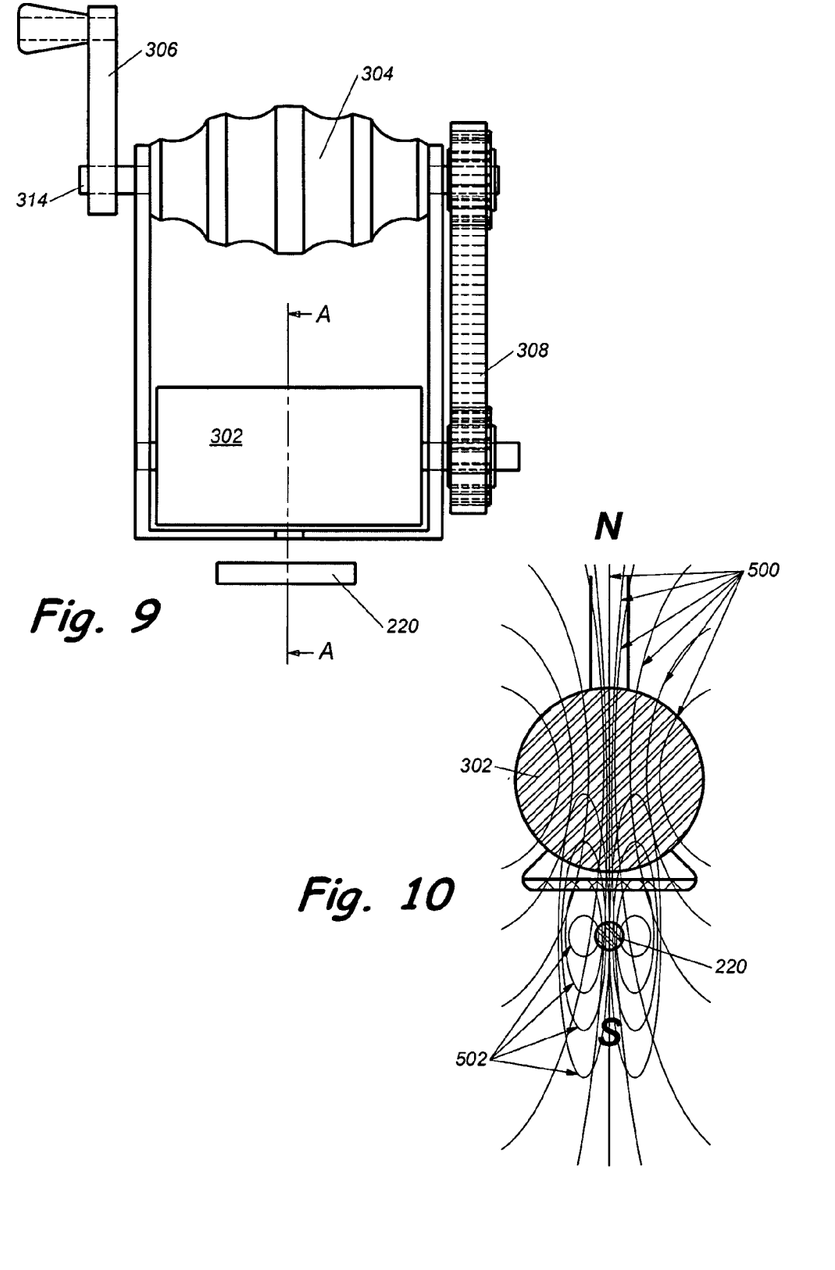
FIG. 9 shows a side view of the actuator and the device shown in FIG. 8.
FIG. 10 is a cross-sectional view of the actuator and the device shown in FIG. 8, showing magnetic flux lines.

In operation, the flange 310 of the actuator 300 is placed against the external surface of a patient's skin in the vicinity of the tension member 201, which is implanted beneath the patient's skin. As shown in FIG. 8, the cylindrical magnet 302 of the actuator 300 rotationally aligns the cylindrical magnet 220 of the tension member 201 such that the north poles N of the cylindrical magnet 302 of the actuator 300 and the cylindrical magnet 220 of the tension member 201 are in the same direction. When the cylindrical magnet 302 of the actuator 300 rotates, a magnetic filed generated by the cylindrical magnet 302 of the actuator 300 causes the cylindrical magnet 220 of the tension member 201 to rotate, which in turn causes the leadscrew 218 of the tension member 201 to rotate so as to cause the tension member 201 to move from a first state to a second state that is different from the first state. In one embodiment, the first state and the second state are corresponding to an extended configuration and a collapsed configuration of the tension member 201, as shown in FIGS. 4 and 5, respectively. The first state of the tension member 201 is characterized by an angle, α, of the axis 203c of the body 203 relative to a horizontal axis, and the second state of the tension member 201 is characterized by an angle, β, of the axis 203c of the body 203 of the tension member 201 relative to the horizontal axis, wherein $0 \leq \alpha < \pi/2$, $0 \leq \beta < \pi/2$, and $\beta \neq \alpha$, as shown in FIGS. 1a and 1b. In one embodiment, when the crank 306 is rotated in a direction 330, it causes the leadscrew 218 of the tension member 201 rotatably to advance into the body 203 of the tension member 201, which pulls the cable 204 into the body 203 of the tension member 201 in a direction arrow 250, as shown in FIG. 8. Therefore, the rotation of the crank 306 indirectly causes change or here reduction of the length L. Conversely, rotation of the crank 306 in the opposite direction increases length L. FIG. 9 shows a side view of the actuator 300 and the cylindrical magnet 220 of the tension member 201. FIG. 10 shows a cross-sectional view of the cylindrical magnet 302 of the actuator 300 and the cylindrical magnet 220 of the tension member 201 having magnet flux lines 500 and 502, respectively.

Referring to FIGS. 13-16, a device 700, which utilizes a toggle mechanism for correction of a spinal deformity, is shown according to an alternative embodiment of the present invention. The device 700 includes a cable 704, a tension member 701, a first engaging member for mechanically engaging the cable 704 with the tension member 701, and a shackle 202 for mechanically engaging the tension member 701 with a pelvic bone.

Figures 13, 14:
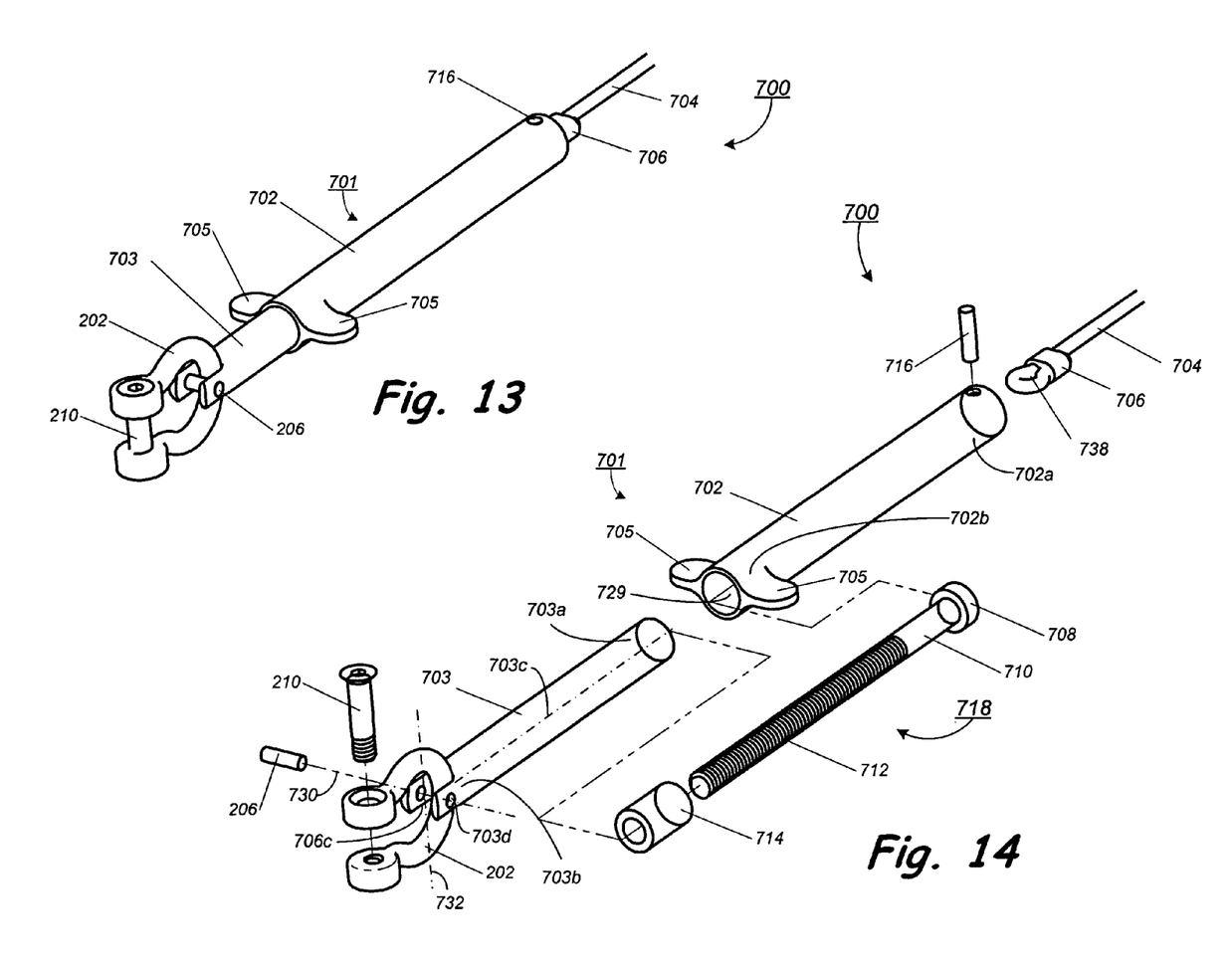
FIG. 13 is a perspective view of a device according to another embodiment of the present invention.
FIG. 14 is a perspective exploded view of the device shown in FIG. 13.

In one embodiment, the tension member 701 has a leadscrew 718 that has a head 708, a shank 710 extending from the head 708, and a threaded portion 712 extending from the shank 710. The tension member 701 further has a one-way clutch 714 coupled with the shank 710. The one-way clutch 714 is configured such that when rotating in one of the clockwise and counterclockwise directions, the one-way clutch 714 engages with the shank 710, and when rotating in the other of the clockwise and counterclockwise directions, the one-way clutch 714 freewheels on the shank 710. The tension member 701 also has a body 703, which has an interior surface complementarily threaded for receiving the leadscrew 718, a first end portion 703a, an opposite, second end portion 703b, an axis 703c, a U-shape cut 703d and a hole 703e formed in the second end portion 703b, where the hole 703e has an axis 730 perpendicular to the axis 703c. Additionally, the tension member 701 has a toggle 702. The toggle 702, in one embodiment, has a first end portion 702a and an opposite, second end portion 702b defining a chamber 729 therebetween for housing the one-way clutch 714 rigidly, a pair of wings 705 radially protruding from the second end portion 702b, and a hole 715 formed on the first end portion 702a.

In one embodiment, as shown in FIG. 14, the first engaging member has a pin 716, and a crimp 706. As assembled, loop portion 738 formed in the first end portion 704a of the cable 704 engages with the pin 716 and is secured with the crimp 706. The first engaging member in another embodiment includes a ball-and-socket joint mechanism.

The device 700 also includes a second engaging member for mechanically engaging the cable 704 with a vertebra (not shown). Preferably, the second engaging member is capable of accommodating changes in the rotational orientation of the cable as curvature is corrected.

The shackle 202 mechanically engages the tension member 701 with a pelvic bone, according to the procedures as described above. Other engaging means of the tension member 701 with the pelvic bone can also be used to practice the present invention.

Figure 15:
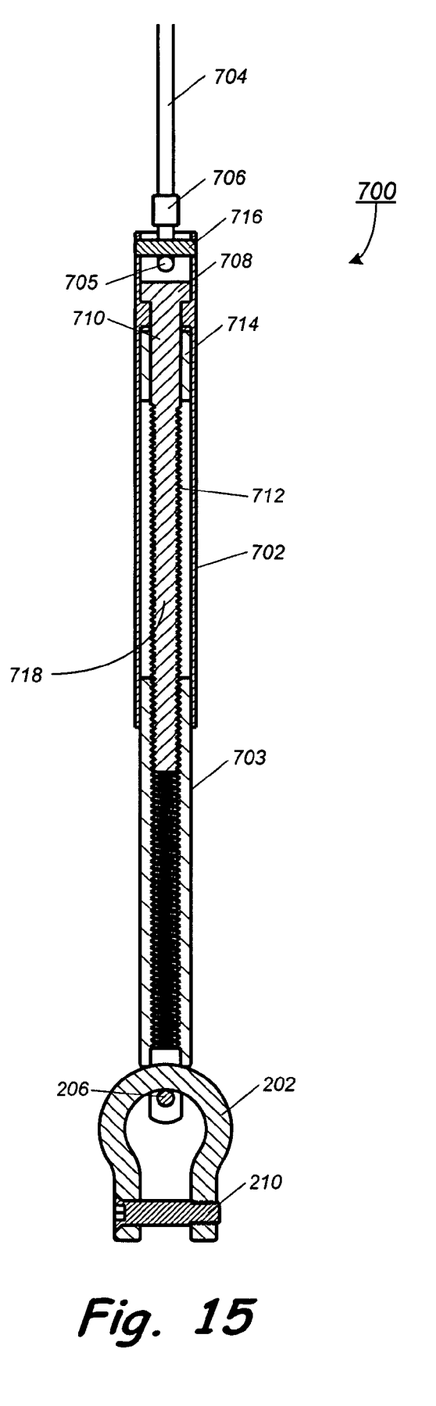
FIG. 15 shows a sectioned view of the device shown in FIG. 13 in an extended configuration.
Figure 16:
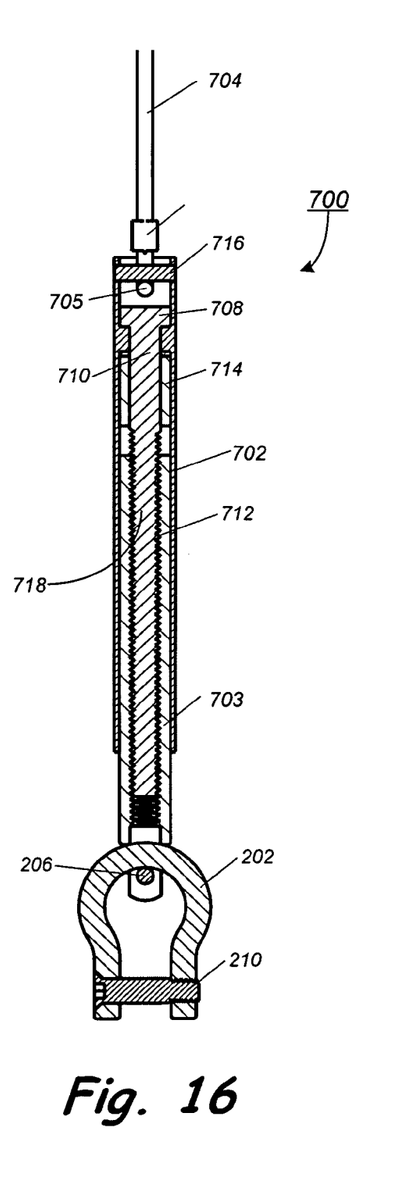
FIG. 16 shows a sectioned view of the device shown in FIG. 13 in a collapsed configuration.

In operation, by pressing alternately on each of the pair of wings 705 of the toggle 703, the one-way clutch 714 rotates alternately in the clockwise and counterclockwise directions thereby causing the leadscrew 718 to rotatably advance into the body 703, which in turn pulls the cable 704 into the body 703 of the tension member 701, whereby the tension of the cable 204 is adjustable for imposing a corrective displacement on the vertebra 100. This operation causes the tension member 201 to move from a first state to a second state that is different from the first state. In one embodiment, the first state and the second state are corresponding to an extended configuration and a collapsed configuration of the tension member 701, as shown in FIGS. 15 and 16, respectively.

In one aspect, the present invention relates to a device for correction of a spinal deformity. In one embodiment, the device includes a cable having a first end portion 204a, and an opposite, second end portion 204b attachable to a vertebra 100, means for adjusting the tension of the cable so as to impose a corrective displacement on the vertebra 100, and means for attaching the body to a pelvic bone 102. In one embodiment, the adjusting means comprise a screw having a threaded portion and engaged with the first end portion of the cable, and a body having an interior surface complementarily threaded for receiving the screw such that when the screw rotatably advances into the body, the tension of the cable is adjusted. The adjusting means includes a magnet driving mechanism, a toggle driving mechanism, a hydraulic driving mechanism, or the likes.

In one embodiment, the cable is made of a biocompatible material. The biocompatible material comprises a polymer, a composite, a metal, an alloy, or any combination thereof. In one embodiment, the cable is coated with a material to reduce abrasion and adhesion of biologic tissues.

In yet a further aspect, the present invention relates to a device for correction of a spinal deformity. In one embodiment, the device includes a tension adjusting member having a first end, a second end, and a body defined therebetween the first end and the second end. The device further includes a tension member having a first end portion, a second end portion and a body portion defined therebetween the first end portion and the second end portion, and movably engaged with the body of the tension adjusting member such that the first end portion of the tension member is movable away from the first end of the tension adjusting member for adjusting the tension of the tension member. In use, the second end portion of the tension member is to be secured to a vertebra 100 and the first end of the tension adjusting member is to be secured to a pelvic bone 102 so that when the first end portion of the tension member is movable away from or toward to the first end of the tension adjusting member, the tension of the tension member is adjusted so as to impose a corrective displacement on the vertebra 100.

A surgical procedure for implantation of the invented device, in one embodiment, includes the following steps: at first, a device having a tension member, a cable engaging with the tension member, and a shackle engaging with the tension member is provided according to one embodiment of the present invention, Then openings at a pelvis bone and a spinal attachment site are incised, respectively. A small hole is drilled through the pelvis bone at a pre-selected position, possibly at or near the iliac crest. The shackle is then secured to the pelvis bone with a screw, clamp or pin. Next, the cable is attached to the spinal attachment site through the openings with an engaging member including bone screws. Once the device is implanted, the wounds are closed and correction of the spinal deformity is performed incrementally and non-invasively according to the procedures as described above.

The present invention, among other unique features, discloses a non-invasive or minimal invasive device (implant) for correcting abnormal spinal curvatures of a patient. One of advantages of the present invention is the potential to correct the abnormal spinal curvatures without spinal fusion. Permanent correction of the abnormal spinal curvatures is achieved by gradually realigning the spinal column so that force imbalances in the spine no longer exist. In certain cases, the onset of skeletal maturity marks the end of curve progression due to the fact that the supporting structures of the spinal column have reacted to the abnormal spinal curvature and imbalances are eliminated. However, in extreme cases of scoliosis the spinal deformity exceeds a critical point and equilibrium may not be reached and therefore the curve progression continues even after the skeletal maturity. It would appear that correcting the curvature and therefore eliminating the imbalances long enough to allow the viscoelastic properties of the supporting structures of the spinal column to react would result in a permanent curvature correction without the need for fusion. However, if the fusion is required, the implanted device would be removed and the fusion would be performed in a procedure known to the people skilled in the art.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A device for correction of a spinal deformity, comprising:
 a. a cable having a first end portion, and an opposite, second end portion;
 b. a tension member having:
  (i). a cylindrical magnet;

(ii). a leadscrew having a helically threaded exterior surface, an interior surface defining a bore for housing the cylindrical magnet rigidly, and an axis therethrough the bore; and (iii). a body having a first end portion and an opposite, second end portion defining a cylindrical chamber therebetween, a longitudinal axis therethrough the cylindrical chamber, and a U-shape cut formed in the second end portion, wherein the cylindrical chamber has a first chamber portion and a second chamber portion neighboring to the first chamber portion, the first chamber portion helically threaded for engaging with the leadscrew such that when the leadscrew is received in the cylindrical chamber, the axis of the leadscrew is substantially coincident with the longitudinal axis of the body and the leadscrew is capable of moving back and forth along the longitudinal axis as being rotated around the longitudinal axis;

c. a shackle having a first end portion, a second end portion and a body portion defined therebetween, wherein the first end portion and the second end portion are configured for being secured to a pelvic bone, and the body portion is received in the U-shape cut of the body such that the tension member is capable of rotating around a first axis and a second axis perpendicular to the first axis, respectively; and d. a first engaging member mechanically engaging the first end portion of the cable with the tension member.

2. The device of claim 1, further comprising means for rotating the leadscrew of the tension member around the axis of the body of the tension member.

3. The device of claim 2, wherein the rotating means comprises an actuator comprising:

a. a first axle and a second axle each having a first end and a second end;

b. a first pulley and a second pulley mounted onto the second end of the first axle and the second end of the second axle, respectively;

c. a cylindrical magnet magnetized diametrically and symmetrically formed on the second axle;

d. a crank attached to the first end of the first axle such that when a torque is applied to the crank to cause the first axle to rotate, a torque is simultaneously applied to the first pulley; and e. a belt engaging with the first pulley and the second pulley for transferring torques from the first pulley to the second pulley so as to rotate the cylindrical magnet.

4. The device of claim 3, wherein in operation, the actuator is positioned such that when the cylindrical magnet of the actuator rotates, a magnetic field generated by the cylindrical magnet of the actuator causes the cylindrical magnet of the tension member to rotate, which in turn causes the leadscrew of the tension member to rotate so as to cause the tension member to move from a first state to a second state that is different from the first state.

5. The device of claim 4, wherein the first state of the tension member is characterized by an angle, $\alpha$, of the axis of the body relative to a horizontal axis, and the second state of the tension member is characterized by an angle, $\beta$, of the axis of the body relative to the horizontal axis, wherein $0 \leq \alpha < \pi/2$, $0 \leq \beta < \pi/2$, and $\beta \neq \alpha$.

6. The device of claim 1, wherein the first chamber portion and the second chamber portion of the cylindrical chamber are sized with a diameter, $d_1$, and $d_2$, respectively, wherein $d_2 > d_1$ such that a step is formed at the junction of the first chamber portion and the second chamber portion.

7. The device of claim 1, wherein the body further has a length, $L_1$, defined therebetween the first end portion and the second end portion.

8. The device of claim 7, wherein the leadscrew further has a first end and an opposite, second end, and a length, $L_2$, defined therebetween, wherein $L_2 < L_1$.

9. The device of claim 8, wherein the tension member further comprises a first cap and a second cap attached to the first end and the second end of the leadscrew, respectively.

10. The device of claim 9, wherein the second cap is sized to fit the second chamber portion of the cylindrical chamber such that as assembled, the second cap prevents the leadscrew from moving out of the cylindrical chamber of the body of the tension member.

11. The device of claim 1, wherein the first engaging member comprises a ball-and-socket joint mechanism.

12. The device of claim 11, wherein the first engaging member comprises:

a. a swaged ball attached to the first end portion of the cable; and b. a pivot cap having a shoulder and a hole formed on the shoulder, wherein as assembled, the first end portion of the cable is received through the hole of the pivot cap and the pivot cap is attached to the first end cap of the tension member such that the swaged ball articulates with the shoulder of the pivot cap, and thus rotating the leadscrew around its axis does not cause the cable to rotate and twist.

13. The device of claim 1, further comprising a second engaging member arranged, in use, mechanically engaging the second end portion of the cable with a vertebra such that the tension of the cable is adjustable for imposing a corrective displacement on the vertebra.

14. The device of claim 13, wherein the second engaging member comprises:

a. a bone screw having a screw head, at least one spherical recess formed on the screw head, a hole formed through the at least one spherical recess, and a body portion having helical threads for threading into the vertebra;

b. a ball having a hole formed therethrough; and c. a crimp, wherein as assembled, the second end portion of the cable is received through the hole in the bone screw and the hole formed in the ball, respectively, and secured by the crimp such that a change in angulation between the tension member and the vertebra is accommodated by articulation of the ball with the spherical recess.

15. The device of claim 13, wherein the second end portion of the cable is formed with a loop portion, and wherein the second engaging member comprises:

a. a pair of bone screws attached to the vertebra;

b. a rod connected with the pair of bone screws; and c. a crimp, wherein as assembled, the loop portion of the second end portion of the cable engages with the rod and is secured with the crimp.

16. The device of claim 1, wherein the first axis and the second axis are perpendicular to the axis of the body of the tension member.

17. The device of claim 1, wherein the shackle is formed in a clevis-shape.

18. The device of claim 1, wherein the cable is made of a biocompatible material.

19. The device of claim 18, wherein the biocompatible material comprises a polymer, a composite, a metal, an alloy, or any combination thereof.

20. The device of claim 19, wherein the cable is coated with a material to reduce abrasion and adhesion of biologic tissues.

21. A method for correcting a spinal deformity, said method comprising the steps of:

providing an implant including:
- a. a cable having a first end portion, and an opposite, second end portion;
- b. a tension member having:
  - (i) a cylindrical magnet;
  - (ii) a leadscrew having a helically threaded exterior surface, an interior surface defining a bore for housing the cylindrical magnet rigidly, and an axis therethrough the bore; and
  - (iii) a body having a first end portion and an opposite, second end portion defining a cylindrical chamber therebetween, a longitudinal axis therethrough the cylindrical chamber, and a U-shape cut formed in the second end portion, wherein the cylindrical chamber has a first chamber portion and a second chamber portion neighboring to the first chamber portion, the first chamber portion helically threaded for engaging with the leadscrew such that when the leadscrew is received in the cylindrical chamber, the axis of the leadscrew is substantially coincident with the longitudinal axis of the body and the leadscrew is capable of moving back and forth along the longitudinal axis as being rotated around the longitudinal axis;
- c. a shackle having a first end portion, a second end portion and a body portion defined therebetween, wherein in use the first end portion and the second end portion are configured for being secured to a pelvic bone, and the body portion is received in the U-shape cut of the body such that the tension member is capable of rotating around a first axis and a second axis perpendicular to the first axis, respectively; and
- d. a first engaging member mechanically engaging the first end portion of the cable with the tension member;

attaching said first and second end portions of said shackle to an extraspinal bone;

attaching said second end portion of said cable to a vertebra; and adjusting said implant without penetrating skin and thereby adjusting a tension of said implant.

* * * * *